United States Patent [19]

Aberg et al.

[11] Patent Number: 4,822,778
[45] Date of Patent: Apr. 18, 1989

[54] MEMBRANE STABILIZING PHENOXY-PIPERIDINE COMPOUNDS AND PHARMACEUTICAL COMPOSITIONS EMPLOYING SUCH COMPOUNDS

[75] Inventors: Gunnar A. K. Aberg, 519 Bergen St., Lawrenceville, N.J. 08648; Bo T. af Ekenstam, Gothenburg, Sweden

[73] Assignee: Gunnar Aberg, Lawrenceville, N.J.

[21] Appl. No.: 148,162

[22] Filed: Jan. 19, 1988

[51] Int. Cl.[4] .................. C07D 211/08; C07D 211/22; A61K 31/445
[52] U.S. Cl. .................................... 514/317; 546/236; 546/240
[58] Field of Search .................. 546/232, 236, 240; 514/317

[56] References Cited

U.S. PATENT DOCUMENTS

| | | | |
|---|---|---|---|
| 3,634,437 | 1/1972 | Todd | 546/197 |
| 3,709,892 | 1/1973 | Leeming et al. | 546/236 |
| 4,225,608 | 9/1980 | Uhl et al. | 514/212 |
| 4,243,807 | 1/1981 | Friebe et al. | 546/232 |

*Primary Examiner*—Alan L. Rotman

[57] ABSTRACT

Compounds of the formula (I)

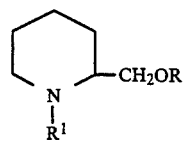

optically active isomers thereof, and/or pharmaceutically acceptable acid addition salts thereof are disclosed, wherein $R^1$ is selected from the group consisting of hydrogen, methyl, ethyl, n-propyl, n-butyl, 2-hydroxyethyl, 3-hydroxypropyl and 4-hydroxybutyl, and wherein R is selected from the group consisting of

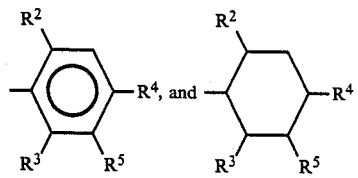

in which $R^2$, $R^3$ $R^4$ and $R^5$ are the same or different and are each independently selected from the group consisting of hydrogen and methyl. Pharmaceutical preparations employing such compounds and method of using such compounds are also disclosed.

12 Claims, No Drawings

MEMBRANE STABILIZING PHENOXY-PIPERIDINE COMPOUNDS AND PHARMACEUTICAL COMPOSITIONS EMPLOYING SUCH COMPOUNDS

The present invention relates to new substituted piperidines, methos for their preparation, and pharmaceutical preparations and methods employing such compounds for membrane stabilization in mammals, including man.

Membrane stabilizing agents, such as lidocaine and mepivacaine, have been shown to possess good local anesthetic effects. These compounds, however, offer short durations of the local anesthetic activity. It would be desirable to provide local anesthetic agents which have a long duration, especially when used as spinal or topical anesthetics, which have therapeutic effects against cardiac arrhythmic conditions, and which can be administered either parenterally or orally.

SUMMARY OF THE INVENTION

It has been found in accordance with the present invention that advantageous membrane stabilizing effects are provided by compounds of the formula (I)

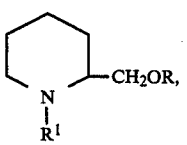

wherein $R^1$ is selected from the group consisting of hydrogen, methyl, ethyl, n-propyl, n-butyl, 2-hydroxyethyl, 3-hydroxypropyl, and 4-hydroxybutyl, and wherein R is selected from the group consisting of a substituted or unsubstituted phenyl group

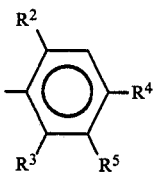

or a substituted or unsubstituted cyclohexyl group

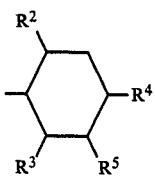

in which $R^2$, $R^3$, $R^4$ and $R^5$ are the same or different and are each selected from the group consisting of hydrogen and methyl. The membrane stabilizing effect of these compounds make them useful as spinal anesthetics, topical anesthetics, local anesthetics, antiarrhythmics, inhibitors of interneurons and antiepileptic agents. The compounds can be administered, for example, topically or perorally as well as in parenteral form. The compounds of the invention can thus be employed in effective amounts to provide such activities in pharmaceutical preparations along with a pharmaceutically acceptable carrier and in methods of treating mammals, such as man.

DETAILED DESCRIPTION OF THE INVENTION

As noted above, $R^1$ in the compounds of the invention can be hydrogen, methyl, ethyl, n-propyl, n-butyl, 2-hydroxyethyl, 3-hydroxypropyl or 4-hydroxybutyl. R can be

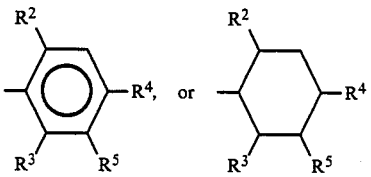

wherein $R^2$, $R^3$, $R^4$ and $R^5$ are the same or different and are each independently selected from hydrogen or methyl. Examples of suitable R groups include 2,6-xylyl, 2,4-xylyl, 2,5-xylyl, 2,4,6-mesityl, phenyl, 2-methylphenyl, and 2,6-dimethylcyclohexyl.

As is evident from the formulas above, the compounds of the invention have an asymmetric center. Thus, they can be resolved into optially active isomers. The present invention includes racemates as well as optically active isomers of the compounds.

The compounds of the invention can be prepared by various processes. For example, a compound of the formula (II)

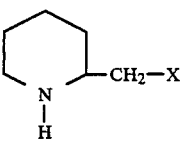

wherein $R^1$ is as defined above and X is a halogen atom other than fluorine can be reacted with a compound of the formula (III)

   MO—R                                     (III)

wherein R is as defined above and M is Na or K. M can also be hydrogen provided a sodium or potassium containing base such as sodium hydroxide, sodium carbonate, etc., is present in the present mixture.

In another method, a picolylhalogenide of the formula (IV)

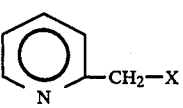

wherein X is as defined above can be reacted with an alkali metal phenolate of the formula

   MO—R                                     (III)

wherein M and R is a substituted or unsubstituted phenyl group as defined above in the presence of a lower alkanol and water to form the compound of the formula (V)

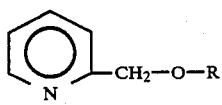

which can be hydrogenated to give a compound of formula (VI)

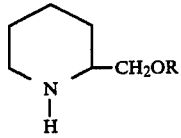

If $R^1$ is to be other than hydrogen, the compound of formula (VI) can then be alkylated or alkoxylated to provide the desired $R^1$ groups. Also, the compound of formula (VI) can be further hydrogenated to give a compound of formula (I) above wherein R is a substituted or unsubstituted cyclohexyl group.

Also, a compound of formula (VII)

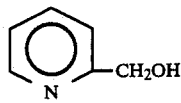

can be reacted with a compound of formula (VIII)

 X—R (VIII)

wherein R is a substituted or unsubstituted cyclohexyl group, and wherein X is as defined above to form a compound of formula (V) which is then hydrogenated. If $R^1$ is to be other than H, the resultant compound of formula (VI) can be alkylated or alkoxylated to provide the desired $R^1$ group.

Further, a compound of the formula (IX)

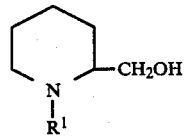

wherein $R^1$ is as defined above can be reacted with a compound of formula (VIII) above wherein R and X are as defined above, to form a compound of formula (I).

In another method, a compound of the formula (X)

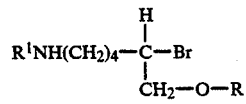

wherein $R^1$ and R are as defined above can be ring-closed in the presence of concentrated hydrochloric acid and at elevated temperature to provide a compound of formula (I).

A compound of the formula (V) above may also be alkylated or alkoxylated and then hydrogenated, for example, according to the following reaction scheme:

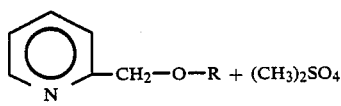

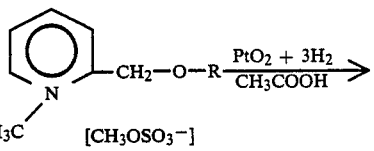

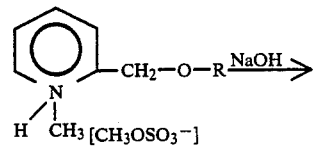

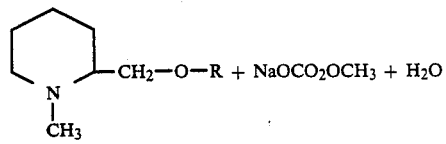

Depending on the process conditions and the starting materials, the end product of these processes can be obtained either as the free base or as the acid addition salt, both of which are included within the scope of the invention. Thus, basic, neutral or mixed salts may be obtained, as well as hemi-, mono-, sesqui- or polyhydrates. The acid addition salts of the compounds of the invention may be transformed in a manner known per se into the free base by using basic agents such as alkali or by ion exchange. On the other hand, the free bases obtained may form salts with organic or inorganic acids. In the prepapration of acid addition salts, preferably such acids are used which form suitable therapeutically acceptable salts. Such acids include hydrohalogen acids; sulfuric acid; phosphoric acid, nitric acid; perchloric acid; aliphatic, alicyclic, aromatic or heterocyclic carboxy or sulfonic acids, such as formic, acetic, propionic, succinic, glycolic, lactic, malic, tartaric, citric, ascorbic, maleic, hydroxymaleic, pyruvic, phenylacetic, benzoic, p-aminobenzoic, anthranilic, p-hydroxybenzoic, salicylic, p-aminosalicyclic, embonic, methanesulfonic, ethanesulfonic, hydroxyethanesulfonic, ethylenesulfonic, halogenbenzenesulfonic, toluenesulfonic, naphthylsulfonic or sulfanilic acids; methionine; tryprophane; lysine; or arginine. These or other salts, e.g., picrates, of the compounds of the invention may serve as purifying agents of the free bases obtained. Salts of the bases may be formed, separated from solution, and then the free base can be recovered from a new salt solution in a purer state.

The starting materials are known or may, if they should be new be obtained according to processes known per se.

In clinical use, the compounds of the invention can be administered topically, orally, rectally or by injection. They may be administered in the form of a pharmaceutical preparation which contains an active component ether as a free base or as a pharmaceutically and biologically acceptable acid addition salt, such as hydrochloride, lactate, acetate, sulfamate, in combination with a pharmaceutically acceptable carrier. The active component is included in the preparation in an amount effective to provide the desired antiarrhythmic, anticonvulsive, interneuronal inhibiting or anesthetic effect. The carrier may be in the form of a solid, semisolid or liquid diluent, or a capsule. Usually the amount of active compound is between 0.1 and 99% by weight of the preparation, between 0.01 and 20% by weight in preparations for injection and between 2 to 99% by weight in preparation for oral administration.

In the preparation of pharmaceutical preparations containing a compound of the present invention in the form of dosage units for oral administration, the compound(s) selected may be mixed with a solid pulverulent carrier, such as lactose, saccharose, sorbitol, mannitol, starch, amylopectin, cellulose derivatives or gelatin, as well as with an antifriction agent such as magnesium stearate, calcium stearate and polyethylene glycol waxes. The mixture is then pressed into tablets. If coated tablets are desired, the above prepared core may be coated with a concentrated solution of sugar, which may contain gum arabic, gelatin, talc, titanium dioxide; or with a lacquer dissolved in volatile organic solvent or mixture of solvents. To this coating, various dyes may be added in order to distinguish among tablets with different active compounds or with different amounts of the active compound present.

Soft gelatin capsules may be prepared which capsules contain a mixture of the active compound or compounds of the invention and vegetable oil. Hard gelatin capsules may contain granules of the active compound in combination with a solid, pulverulent carrier such as lactose, saccharose, sorbitol, mannitol, potato starch, corn starch, amylopectin, cellulose derivatives or gelatin.

Dosage units for rectal administration may be prepared in the form of suppositories which contain the active substance in a mixture with a neutral fat base, or they may be prepared in the form of gelatin-rectal capsules which contain the active substance in a mixture with a vegetable oil or paraffin oil.

Liquid preparations for oral administration may be prepared in the form of syrups or suspension, e.g., solutions containing from 0.2% to 20% by weight of the active ingredient and the remainder consisting of sugar and a mixture of ethanol, water, glycerol and propylene glycol. If desired, such liquid preparations may contain coloring agents, flavoring agents, saccharin and carboxymethylcellulose as a thickening agent.

Solutions for parenteral administration by injection may be prepared as aqueous solutions of a water soluble, pharmaceutically acceptable salt of the active compound, preferably in a concentration from 0.01% to 10% by weight. These solutions may also contain stabilizing agents, agents that affect the duration of the therapeutic effect, such a vasoconstrictors (e.g., vasopressin or derivatives), dextranes, potassium ions, Na benzoate, agents that affect the weight of the solutions, such as sugars, and/or buffering agents and may be manufactured in different dosage units.

The precise dosage administered will depend upon the intended application, i.e., as a spinal anesthetic, topical anesthetic, local anesthetic, antiarrhythmic, interneuronal inhibitor and/or antiepiletic. Typically, as a spinal anesthetic and local anesthetic, the compounds of the invention will be employed as from about 0.1 to about 10% by weight solutions. The topical anesthetic used in the compounds are from, for example, from example 0.1 to about 20% by weight of the preparation, e.g., a cream or lotion. For antiarrhythmic, interneuronal inhibitors and anticonvulsive applications, the compound of the invention may be administered by single or repeated parental or oral administration of from about 20 to about 1,000 mg of the compound, with the actual dosage being titrated to the individual.

The following examples are intended to illustrated but not to limit the invention. Temperature is given in degrees Centigrade.

EXAMPLE 1

Two hundred and forty-five (245) g of 2,6-xylenol were transformed into the potassium salt thereof by reacting with 113 g of KOH in 545 mls of water.

To this solution were added dropwise 139 g of 2-chloromethyl pyridine hydrochloride dissolved in 1470 mls of methanol. The reaction was carried out for 2 hours at boiling temperature. The mixture was cooled to 15° C., treated with 5 g of active carbon, and filtered. The filtrate was evaporated in vacuo and the residue was distilled in vacuo at about 2 mm Hg and 140° C. The product obtained was 2-[(2,6-xyloxy)-methyl]pyridine.

Twenty-nine (29) g of 2-[(2,6-xyloxy)methyl]pyridine were hydrogenated in 250 mls of concentrated acetic acid using hydrogen in the presence of 1.0 g of $PtO_2$. The hydrogenation took place by introducing hydrogen to theoretical volume at 70°–80° C. in an autoclave at a pressure of 5–10 atmospheres. The catalyst was filtered off, and the acetic acid evaporated. Twenty-four (24) g of 2-[(2,6-xyloxy)methyl]piperidine were obtained. The acetic acid salt produced was dissolved in 300 mls of water and was purified with active carbon, whereupon the product was precipitated as the base using ammonia. The base product was dried and dissolved in 150 mls of methyl ethyl ketone, whereupon the hydrochloride was obtained by neutralizing with dry HCl. The hydrochloride of 2-[(2,6-xylyoxy)methyl]piperidine melted at 227°–229° C.

EXAMPLE 2

Fifty-eight (58) g of 2-[(2,6-xyloxy)methyl]pyridine were added to 276 mls of xylene and were reacted with 26.4 mls of dimethylsulfate for 4 hours at 130° C. After isolation, purification and hydrogenation according to Example 1, 49 g of N-methyl-2-[(2,6-xyloxy)methyl]-piperidine hydrochloride were obtained having a melting point of 171°–173° C.

EXAMPLES 3 AND 4

The procedures of Examples 1 and 2 were repeated, but with the introduction of hydrogen being continued at an elevated temperature of 100° C. and an increased pressure of about 10 atmospheres. By this process, the corresponding 2-[(2,6-dimethylcyclohexyloxy)methyl]-piperidine (Example 3) and N-methyl-2-[(2,6-dimethylcyclohexyl)methyl]piperidine (Example 4) were obtained. Melting points of 155°–157° C. and 162° C., respectively, were obtained for these compounds as their hydrochlorides.

EXAMPLE 5

By exchanging dimethylsulfate in Example 2 above with diethylsulfate, N-ethyl-2-[(2,6-xyloxy)-methyl]-piperidine is obtained, m.p. 163°–164° C. (HCl).

EXAMPLE 6

N-(n-propyl)-2-[(2,6-xyloxy)methyl]piperidine was prepared in accordance with the procedure of Example 2 by employing dipropylsulfate in place of dimethylsulfate. The product has a melting point of 167°-168.5° (HCl).

EXAMPLE 7

N-(n-butyl)-2-[(2,6-xyloxy)methyl]piperidine was prepared by reacting n-butylaldehyde and the pyridine produced in Example 1. The N-(n-butyl)-2-[(2,6-xyloxy)methyl]piperidine had a melting point of 154° C. (base).

EXAMPLES 8-12

In accordance with the foregoing, the following compounds of formula I above having a substituted or unsubstituted phenyl R group were also prepared as indicated in Table 1 below:

TABLE 1

| Example | $R^1$ | $R^2$ | $R^3$ | $R^4$ | $R^5$ | Melting Point |
|---|---|---|---|---|---|---|
| 8 | $CH_3$ | $CH_3$ | H | $CH_3$ | H | 174° C. (base) |
| 9 | $CH_3$ | $CH_3$ | H | H | $CH_3$ | 174° C. (base) |
| 10 | $CH_3$ | H | H | H | H | 166° C. (base) |
| 11 | $CH_3$ | $CH_3$ | H | H | H | 172° C. (base) |
| 12 | $HOC_2H_4$ | $CH_3$ | $CH_3$ | H | H | 135° C. (base) |

EXAMPLE 13

N-methyl-2-[(2,6-xyloxy)methyl]piperidine can be obtained by ring-closing an aliphatic compound in accordance with the following.

One hundred (100) g of 1-(δ-methylaminobutyl)-1-bromo-2-(2,6-xyloxy)ethane are ring-closed while being boiled in 300 g of concentrated hydrochloric acid for 4 hours. Five (5) g of active carbon are added and the solution is allowed to cool during stirring for 0.5 hour. The solution is then cooled to about 15° C., is filtered and is evaporated to dryness. The residue is dissolved in 500 mls of water and is neutralized using a solution of NaOH. N-methyl-2-[(2,6-xyloxy)methyl]piperidine is extracted from the sodium chloride mixture using 2×150 mls of ligroin, which given the compound as an oil after evaporation in vacuo. The base obtained can be further purified by treatment with active compound and by filtration when dissolved in 300 mls of methyl ethyl ketone.

EXAMPLE 14

The following procedure can be used to prepare N-methyl-2-[(2,6-xyloxy)methyl]piperidine hydrochloride:

Two hundred (200) g of 2-[(2,6-xyloxy)methyl]-pyridine are mixed with 300 g of dimethylsulphate whereupon 500 g of water are added at 100° C. during 3 hours. The excess of dimethylsulfate is removed by extraction using ether. The remaining solution is purified using active carbon and the resultant solution filtered. N-methyl-2-[(2,6-xyloxy)methyl]pyridine methylsulfate is isolated as a salt by evaporation of the water in vacuo.

Fifty (50) g of this quaternary compound are dissolved in 150 g of concentrated acetic acid and 1 g of platinum oxide is added. Hydrogenation with hydrogen gas is carried out at 600-800 kPa and 60°-70° C. until the calculated amount of hydrogen is absorbed. The catalyst is filtered off and the acetic acid is distilled off in vacuo. The residue is dissolved in 250 g of water and is treated with active carbon (1 g), which then is filtered off. The filtrate is treated with a 10% solution of NaOH to pH 8, whereby the base precipitates and is isolated by means of extraction using 2×100 mls of ether. The pure base is dissolved in 200 mls of methyl ethyl ketone whereupon the hydrochloride is precipitated by introducing gaseous HCl.

EXAMPLE 15

A syrup containing 2% (weight per volume) of active substance can be prepared from the following ingredients:

| | |
|---|---|
| 2-[(2,6-xyloxy)methyl]piperidine-HCl | 2.0 g |
| Saccharine | 0.6 g |
| Sugar | 30.0 g |
| Glycerine | 5.0 g |
| Flavoring agent | 0.1 g |
| Ethanol 96% | 10.0 g |
| Distilled water added to | 100.0 ml |

Sugar, saccharine and the active ether salt are dissolved in 60 g of warm water. After cooling, glycerine and a solution of flavoring agents dissolved in ethanol are added. To the mixture, water is then added to 100 ml.

The active substance in the above formulation may be replaced with other pharmaceutically acceptable acid addition salts in accordance with the invention.

EXAMPLE 16

N-methyl-2-[(2,6-xyloxy)methyl]piperidine hydrochloride (250 g) is mixed with lactose (175.8 g) potatoe starch (169.7 g) and colloidal silic acid (32 g). The mixture is moistened with a 10% solution of gelatine and is granulated through a 12-mesh sieve. After drying, potatoe starch (160 g), talc (50 g) and magnesium stearate (5 g) are admixed and the mixture thus obtained is pressed into tablets (10,000) which contain 25 mg of active substance each. The tablets can be sold on the market provided with a breaking score to give another dose than 25 mg or to give multiples thereof when broken.

EXAMPLE 17

Granules are prepared from N-ethyl-2-[(2,6-xyloxy)-methyl]piperidine hydrochloride (250 g), lactose (175.9 g) and an alcoholic solution of polyvinyl pyrrolidone (25 g). After drying, the granules are mixed with talc (25 g), potatoes starch (40 g) and magnesium stearate (2.50 g) and are pressed into 10,000 tablets being biconvex. These tablets are coated with a primary coating of 10% alcoholic solution of shellac and thereupon with a series of coating with an aqueous solution containing saccharose (45%), gum arabicum (5%), gelatine (4%) and dyestuff (0.2%). Talc and powder sugar are used for powdering after the first five coatings. The resultant coating is then further coated with a 66% sugar syrup and is polished with a 10% carnaube wax solution in carbon tetrachloride.

EXAMPLE 18

N-(n-propyl)-2-[(2,6-xyloxy)methyl]piperidine hydrochloride (1 g), sodium chloride (0.8 g) and ascorbic acid (0.1 g) are dissolved in sufficient amount of distilled water to give 100 ml of solution. This solution, which contains 10 mg of active substance on each ml, is used in filling ampoules, which are sterilized by heating at 120° C. for 20 minutes.

BIOLOGICAL EFFECTS

Toxicology

The compounds according to Examples 1–12, lidocaine and bupivacaine have been tested as to their toxicological effects in mice. $LD_{50}$-values are given in Table 2 below for subcutaneous administration.

TABLE 2

$LD_{50}$-values in mice

| Compound according to Example | $LD_{50}$ (s.c.) mg/kg |
|---|---|
| 1 | 110 |
| 2 | 260 |
| 3 | 180 |
| 4 | 350 |
| 5 | 200 |
| 6 | 200 |
| 7 | 225 |
| 8 | 400 |
| 9 | 400 |
| 10 | 150 |
| 11 | 300 |
| 12 | 220 |
| Lidocaine | 220 |
| Bupivacaine | 50 |

Convulsive doses and lethal doses after intravenous administration for selected compounds of the invention and for Bupivacaine are shown in Table 3 below.

TABLE 3

Convulsive and lethal doses of selected compounds administered intravenously at 1.0 mg/kg/min to rats (male; 250–300 g).

| Compound according to Example | Convulsive dose mg/kg | Lethal dose mg/kg |
|---|---|---|
| 1 | 22 | 50 |
| 2 | 10 | 33 |
| 5 | 15 | 41 |
| 6 | 11 | 20 |
| 7 | 16 | 24 |
| Bupivacaine | 9 | 13 |

Pharmacology

1. Local anesthetic effects of the compounds of Examples 1–12 above were determined as discussed below.

A. Infiltration anesthetic effects:

The effects of the new compounds were tested according to Aberg & Sydnes, *Acta Anaesth. Scand.*, 1975, 19, 377 after intracutaneous injection of 0.2 ml of the test solutions to guinea pigs. The results are given in Table 4 below.

B. Nerve blocking effects.

The tests were carried out in vivo in rats after injection of 0.25 ml of the test solutions close to the sciatic nerve. The results are given in Table 4 below.

C. Topical anesthetic effects.

Corneal tests were carried out in rabbits in vivo according to Henn. *Acta Anaeth. Scand.*, 1960, 4, 125, after application of 0.25 ml of the test solutions into the conjunctival sacs of the animals. The results are given in Table 5 below.

TABLE 4

Local anesthetic effects of solutions containing 0.5% by weight of the compound.

| Compound according to Example | Infiltration anesthesia duration (min) | Nerve blocking effect Sensoric blockade (min) | Nerve blocking effect Motoric blockade (min) |
|---|---|---|---|
| 1 | 40 | 90 | 75 |
| 2 | 120 | 135 | 110 |
| 3 | 35 | 0 | 0 |
| 4 | 60 | 80 | 65 |
| 5 | 70 | 115 | 90 |
| 6 | 175 | 155 | 145 |
| 7 | 165 | 160 | 140 |
| 8 | 35 | 75 | 55 |
| 9 | 25 | 95 | 75 |
| 10 | 35 | 40 | 25 |
| 11 | 55 | 85 | 60 |
| 12 | 40 | 95 | 95 |
| Lidocaine | 25 | 35 | 40 |

TABLE 5

Topical anesthetic effects on rabbit cornea

| Compound according to Example | Concentration (%) | Onset frequency | Duration (min) |
|---|---|---|---|
| 1 | 1.0 | 9/10 | 24 ± 4 |
| 2 | 1.0 | 7/10 | 14 ± 4 |
| 5 | 1.0 | 9/10 | 18 ± 3 |
| 6 | 1.0 | 9/9 | 24 ± 2 |
| 7 | 1.0 | 10/10 | 27 ± 4 |
| Lidocaine | 4.0 | 10/10 | 23 ± 3 |

D. Spinal Anesthetic Effects.

Spinal anesthetsias were performed on cynomolgus monkeys that had been sedated with ketamine (6 mg/kg; i.m.). 1.0 ml of the test solutions were injected intrathecally and the durations were tested every ten (10) minutes with forceps. The duration of motoric blockade was calculated as the time until the hind leg paralysis ceased. The results are shown in Table 6 below.

TABLE 6

Spinal Anesthetic Effects in Monkeys

| Compound According to Ex. No. | No. of Monkeys Tested | Solution Conc. (% by wt.) | Duration in minutes Anal Blockade | Duration in minutes Digital Blockade | Duration in minutes Motor Blockade |
|---|---|---|---|---|---|
| 5 | 6 | 3.0 | 258 | 163 | 178 |
| 6 | 12 | 3.0 | >291 | 222 | >198 |
| Lidocaine | 6 | 5.0 | 150 | 88 | 73 |

2. Antiarrhythmic effects.

Ventricular arrhythmias were induced in anesthetized dogs by intravenous injection of ouabain: initially 40 μg/kg bodyweight and thereafter 20 μg/kg bodyweight every 20 minutes until the ventricular arrhythmia was regarded as manifest. Thereupon, the test compounds were administered intravenously in the doses indicated in Table 7. Lidocaine was also tested by the same procedure. The results are given in Table 7 below. The new compounds were compared with lidocaine, a known antiarrhythmic compound.

TABLE 7

Antiarrhythmic effects in anesthetized dogs.

| Compound of Ex. No. | Dose (mg/kg) | No. of tests | Duration of regularization (min) |
|---|---|---|---|
| 1 | 1 | 5 | 5 |
| 1 | 2 | 5 | 10 |

TABLE 7-continued

Antiarrhythmic effects in anesthetized dogs.

| Compound of Ex. No. | Dose (mg/kg) | No. of tests | Duration of regularization (min) |
|---|---|---|---|
| 2 | 1 | 5 | 2 |
| 2 | 2 | 5 | 4 |
| 5 | 1 | 3 | 3 |
| 6 | 1 | 3 | 4 |
| 7 | 1 | 3 | 4 |
| Lidocaine | 1 | 5 | 2 |
| Lidocaine | 2 | 5 | 4 |

3. Interneuronblocking effects.

Tests were carried out in anesthetized cats (female; 2.5-3.5 kg bodyweight). The effects of the compounds were studied on the lingomandibular reflex, which was provoked by means of electrical stimulation of the tongue. The mandibular reflux was registered from a transducer connected to the mandible. The compounds were administered intravenously in the doses indicated in Table 8. Phenyramidole was tested by the same procedure. As evident from the results shown in Table 8, the compound according to Example 2 of the invention is 10 times as potent as phenyramidole.

TABLE 8

| Compound according to Example | Dose mg/kg bodyweight | Maximal inhibition % | Duration of inhibition (min.) |
|---|---|---|---|
| 2 | 0.25 | 30 | 10 |
| 2 | 0.50 | 80 | 20 |
| 2 | 1.00 | 100 | 45 |
| Phenyramidole | 2.5 | 40 | 5 |
| Phenyramidole | 5.0 | 80 | 20 |
| Phenyramidole | 10.0 | 100 | 60 |

It will be understood that the embodiments described above are merely exemplary and that persons skilled in the art may make many variations and modifications without departing from the spirit and scope of the invention. All such modifications and variations are intended to be included within the scope of the invention as defined by the appended claims.

What is claimed is:

1. A compound of the formula (1)

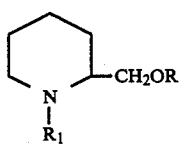
(1)

or an optically active isomer thereof or a pharmaceutically acceptable acid addition salt thereof, wherein $R_1$ is selected from the group consisting of hydrogen, methyl, ethyl, n-propyl, n-butyl, 2-hydroxyethyl, 3-hydroxypropyl or 4-hydroxybutyl, and wherein R is selected from the group consisting of

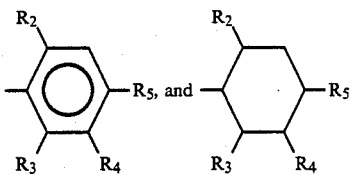

in which $R_2$ and $R_3$ are both methyl, $R_4$ and $R_5$ are the same or different and are each independently selected from the group consisting of hydrogen and methyl.

2. A compound according to claim 1, wherein R is the group

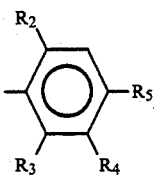

in which $R_2$ and $R_3$ are methyl and $R_4$ and $R_5$ are hydrogen.

3. A compound according to claim 1, which is N-(n-propyl)-2-[(2,6-xyloxy)methyl]piperidine, or an optically active isomer thereof or a pharmaceutically acceptable acid addition salt thereof.

4. A compound according to claim 1, which is N-ethyl-2-[(2,6-xyloxy)methyl]piperidine, or an optically active isomer thereof or a pharmaceutically acceptable acid addition salt thereof.

5. A method for membrane stabilization in mammals, said method consists of administering to a mammal in need thereof an anesthetically effective amount of a compound of the formula (1)

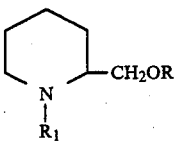
(1)

or an optically active isomer thereof or a pharmaceutically acceptable acid addition salt thereof, wherein $R_1$ is selected from the group consisting of hydrogen, methyl, ethyl, n-propyl, n-butyl, 2-hydroxyethyl, 3-hydroxypropyl or 4-hydroxybutyl, and wherein R is selected from the group consisting of

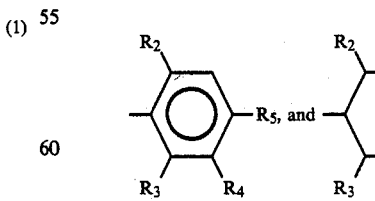

in which $R_2$ and $R_3$ are both methyl, $R_4$ and $R_5$ are the same or different and are each independently selected from the group consisting of hydrogen and methyl.

6. A method according to claim 5, wherein R in said active compound is the group

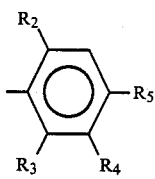

in which $R_2$ and $R_3$ are methyl and $R_4$ and $R_5$ are hydrogen.

7. A method according to claim 5, wherein said active compound is N-(n-propyl)-2-[(2,6-xyloxy)-methyl) piperidine, or an optically active isomer thereof or a pharmaceutically acceptable acid addition salt thereof.

8. A method according to claim 29, wherein said active compound is N-ethyl-2-[(2,6-xyloxy)-methyl) piperidine, or an optically active isomer thereof or a pharmaceutically acceptable acid addition salt thereof.

9. A pharmaceutical composition consisting of an antiarrhythmically effective amount of a compound of the formula (1)

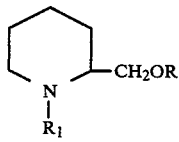 (1)

or an optically active isomer thereof or a pharmaceutically acceptable acid addition salt thereof, wherein $R_1$ is selected from the group consisting of hydrogen, methyl, ethyl, n-propyl, n-butyl, 2-hydroxyethyl, 3-hydroxypropyl or 4-hydroxybutyl, and wherein R is selected from the group consisting of

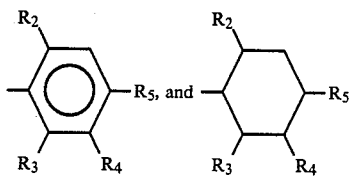

in which $R_2$ and $R_3$ are both methyl, $R_4$ and $R_5$ are the same or different and are each independently selected from the group consisting of hydrogen and methyl, together with a pharmaceutically acceptable carrier.

10. A pharmaceutical composition consisting of an anticonvulsive effective amount of a compound of the formula (1)

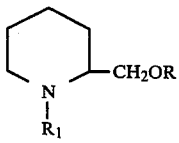 (1)

or an optically active isomer thereof or a pharmaceutically acceptable acid addition salt thereof, wherein $R_1$ is selected from the group consisting of hydrogen, methyl, ethyl, n-propyl, n-butyl, 2-hydroxyethyl, 3-hydroxypropyl or 4-hydroxybutyl, and wherein R is selected from the group consisting of

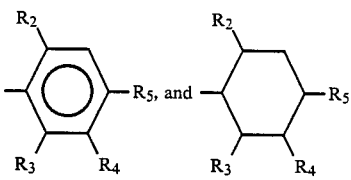

in which $R_2$ and $R_3$ are both methyl, $R_4$ and $R_5$ are the same or different and are each independently selected from the group consisting of hydrogen and methyl, together with a pharmaceutically acceptable carrier.

11. A method for membrane stabilization in mammals, said method consisting of administering to a mammal in need thereof an antiarrhythmically effective amount of a compound of the formula (1)

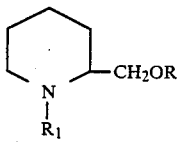 (1)

or an optically active isomer thereof or a pharmaceutically acceptable acid addition salt thereof, wherein $R_1$ is selected from the group consisting of hydrogen, methyl, ethyl, n-propyl, n-butyl, 2-hydroxyethyl, 3-hydroxypropyl or 4-hydroxybutyl, and wherein R is selected from the group consisting of

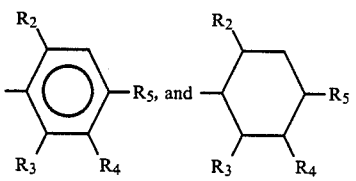

in which $R_2$ and $R_3$ are both methyl, $R_4$ and $R_5$ are the same or different and are each independently selected from the group consisting of hydrogen and methyl, together with a pharmaceutically acceptable carrier.

12. A method for membrane stabilization in mammals, said method consisting of administering to a mammal in need thereof an antconvulsive effective amount of a compound of the formula (1)

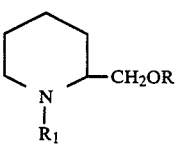 (1)

or an optically active isomer thereof or a pharmaceutically acceptable acid addition salt thereof, wherein $R_1$ is selected from the group consisting of hydrogen, methyl, ethyl, n-propyl, n-butyl, 2-hydroxyethyl, 3-hydroxypropyl or 4-hydroxybutyl, and wherein R is selected from the group consisting of

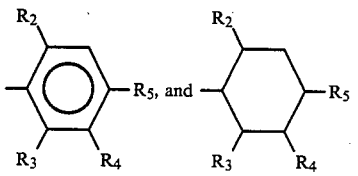

in which $R_2$ and $R_3$ are both methyl, $R_4$ and $R_5$ are the same or different and are each independently selected from the group consisting of hydrogen and methyl, together with a pharmaceutically acceptable carrier.

* * * * *